US009403892B2

(12) United States Patent
Zhou et al.

(10) Patent No.: US 9,403,892 B2
(45) Date of Patent: Aug. 2, 2016

(54) THERAPEUTIC TRAIL FUSION PROTEIN AND PREPARATION AND USE THEREOF

(71) Applicant: Magellan Pharma Co. Ltd., Nanjing (CN)

(72) Inventors: Bing Zhou, Yantai (CN); Yu Zhou, Yantai (CN); Jing Jiang, Yantai (CN)

(73) Assignee: MAGELLAN PHARMA CO. LTD., Nanjing (CN)

( * ) Notice: Subject to any disclaimer, the term of this patent is extended or adjusted under 35 U.S.C. 154(b) by 0 days.

(21) Appl. No.: 14/165,555

(22) Filed: Jan. 27, 2014

(65) Prior Publication Data
US 2014/0206843 A1 Jul. 24, 2014

Related U.S. Application Data

(63) Continuation of application No. PCT/CN2012/079233, filed on Jul. 27, 2012.

(30) Foreign Application Priority Data

Jul. 28, 2011 (CN) .......................... 2011 1 0213943

(51) Int. Cl.
| | | |
|---|---|---|
| *C07K 14/52* | (2006.01) | |
| *A61K 38/17* | (2006.01) | |
| *A61K 38/19* | (2006.01) | |
| *C12P 21/02* | (2006.01) | |
| *C12N 5/10* | (2006.01) | |
| *C12N 15/09* | (2006.01) | |
| *C07K 14/705* | (2006.01) | |
| *C12N 15/63* | (2006.01) | |
| *A61K 38/00* | (2006.01) | |

(52) U.S. Cl.
CPC ........... *C07K 14/52* (2013.01); *C07K 14/70575* (2013.01); *A61K 38/00* (2013.01); *A61K 38/17* (2013.01); *A61K 38/19* (2013.01); *A61K 38/191* (2013.01); *C07K 2319/73* (2013.01); *C12N 5/10* (2013.01); *C12N 15/63* (2013.01); *C12P 21/02* (2013.01)

(58) Field of Classification Search
None
See application file for complete search history.

(56) References Cited

U.S. PATENT DOCUMENTS

| | | | | |
|---|---|---|---|---|
| 5,350,836 | A * | 9/1994 | Kopchick et al. | 530/399 |
| 6,284,236 | B1 * | 9/2001 | Wiley et al. | 424/85.1 |
| 6,642,358 | B1 * | 11/2003 | Rauch et al. | 530/350 |
| 7,662,367 | B2 * | 2/2010 | Desjarlais et al. | 424/85.1 |
| 2004/0014948 | A1 * | 1/2004 | Halkier et al. | 530/388.22 |

OTHER PUBLICATIONS

Jiang et al. GMP production and characterization of leucine aipper-tagged tumor necrosis factor-related apoptosis-inducing ligand (LZ-TRAIL) for phase I clinical trial. Eur J Pharmacol 740: 722-732, 2014.*
Lincz et al. TRAIL-induced eradication of primary tumour cells from multiple myeloma patient bone marrows is not related to TRAIL receptor expression or prior chemotherapy. Leukemia 15: 1650-1657, 2001.*
Plasilova et al. TRAIL (Apo2L) suppresses growth of primary human leukemia and myelodysplasia progenitors. Leukemia 16: 67-73, 2002.*
Rozanov et al. Engineering a leucine zipper-TRAIL homotrimer with improved cytotoxicity in tumor cells. Mol Cancer Ther 8(6): 1515-1525, 2009.*
Shah et al. Inducible release of TRAIL fusion proteins from a proapoptotic form for tumor therapy. Cancer Res 64: 3236-3242, 2004.*
Walczak et al. Tumoricidal activity of tumor necrosis factor-related apoptosis-inducing ligand in vivo. Nature Med 5(2): 157-163, 1999.*
Walczak et al. TRAIL-R2: a novel apoptosis-mediating receptor for TRAIL. EMBO J 16(17): 5386-5397, 1997.*
Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Kaufman et al. Transgenic analysis of a 100-kb human beta-globin cluster-containing DNA fragment propagated as a bacterial artificial chromosome. Blood 94(9): 3178-3184, 1999.*
McBurney et al. Evidence for repeat-induced gene silencing in cultured mammalian cells: inactivation of tandem repeats of transfected genes. Exp Cell Res 274: 1-8, 2002.*
Wang et al. Rapid analysis of gene expression (RAGE) facilitates universal expression profiling. Nucleic Acids Research 27(23): 4609-4618, 1999.*
Williams et al. BMC Biotechnol 5:17, 2005.*
Tokuriki et al. Stability effects of mutations and protein evolvability. Curr Opin Structural Biol 19: 596-604, 2009.*

* cited by examiner

*Primary Examiner* — Bridget E Bunner
(74) *Attorney, Agent, or Firm* — Jun He Law Offices P.C.; Jay Z. Zhang

(57) ABSTRACT

This invention relates to the biotechnology area, and provides a kind of TRAIL chimeric protein, DNA sequence encoding this chimeric protein, vectors comprising this DNA, host cells or transgenic animals that contain one of the vectors, and preparation methods for the said chimeric protein and its applications. The said TRAIL fusion protein from the N to C terminal comprises human leucine zipper sequence, human TRAIL protein, human TRAIL extracellular domain or a fragment thereof. The chimeric protein has significantly enhanced stability, prolonged half-life in animals, increased efficacy and thus has broad application future.

14 Claims, 5 Drawing Sheets

THERAPEUTIC TRAIL FUSION PROTEIN AND PREPARATION AND USE THEREOF

CROSS-REFERENCE TO RELATED APPLICATIONS

This application is a continuation of the International Application No. PCT/CN2012/079233 filed Jul. 27, 2012 claiming the priority of Chinese Patent Application No. 201110213943.9 filed on Jul. 28, 2011.

FIELD OF THE INVENTION

This invention generally relates to therapeutic proteins, and specifically relates to a chimeric protein of tumor necrosis factor-related apoptosis-inducing ligand (TRAIL), its preparation and use thereof for disease treatment.

BACKGROUND OF THE INVENTION

Cancer is a category of severe diseases affecting human health, and its treatment is becoming a huge and imminent public issue awaiting more effective therapies. Although much progress has been made recently in anticancer drug research, the unfavorable specificity and harmful side effects to normal cells limit their applications. Therefore, genetic engineering drugs for targeted cancer therapy are still well welcomed due to potential social and economic benefits.

In 1995, Wiler S R et al. reported the finding of a new gene from expressed sequence tag (EST) library coding for a new antitumor protein, human tumor necrosis factor-related apoptosis-inducing ligand (TRAIL or Apo2L), belonging to the Tumor Necrosis Factor superfamily (Wiley S R, et al., Immunity 3:673-682, 1995). After TRAIL binding to DR4 or DR5, the death domains of the receptors pass the apoptosis signaling through FADD and caspase 8. TRAIL inhibits the growth of and is cytotoxic to most malignant cancer cell lines, however, normal cells are largely refractory to its apoptotic cytotoxicity (Ashkenazi A, et al., J Clin Invest 104:155-162, 1999). Because of its specific apoptotic activity against cancer but not to normal cells, TRAIL holds great promises in anticancer treatment and has been a hot research spot. Although TRAIL has demonstrated significant in vitro and in vivo as well as clinical tumor-inhibitory activities, its half life is relatively short, with a $T_{1/2}$ of about 40 minutes in human, seriously compromising its in vivo efficacy.

SUMMARY OF THE INVENTION

The present invention provides a chimeric human TRAIL protein with a substantially increased stability and significantly longer half-life in animals. The chimeric TRAIL protein thus can have a substantially improved therapeutic efficacy.

Specifically, the chimeric human TRAIL protein of the present invention includes (1) a human leucine zipper domain; and (2) a human TRAIL protein, a human extracellular domain or a fragment of the extracellular domain.

TRAIL (TNF-related apoptosis-inducing ligand) is a protein generally known in the art. The TRAIL gene sequence is shown under GenBank Accession No. NM_003810. TRAIL functions as a ligand and binds to the death receptors DR4 (TRAIL-R1) and DR5 (TRAIL-R11), whereby inducing apoptosis or cell death. The amino acid sequence of human TRAIL protein is shown in SEQ ID NO:6. The extracellular domain is from the N terminal amino acid No. 43 to No. 281, as shown in SEQ ID NO:7.

In accordance with the present invention, a chimeric human TRAIL protein is provided having from N-terminal to C-terminal direction: (1) a human leucine zipper domain; (2) optionally a linker having no more than 10 amino acid residues; and (3) a human TRAIL protein, extracellular domain or a fragment thereof, capable of binding to the death receptor DR4 (TRAIL-R1) or DR5 (TRAIL-R11).

For purposes of the present invention, the human TRAIL polypeptide in the chimeric protein can be all or a part of the natural TRAIL protein so long as it can bind to the death receptor DR4 (TRAIL-R1) or DR5 (TRAIL-R11). Preferably, the human TRAIL polypeptide in the chimeric protein can be the human TRAIL extracellular domain, comprising all or a part of the extracellular domain of the native human TRAIL protein. More preferably, the human TRAIL polypeptide in the chimeric protein is a soluble TRAIL fragment comprising all or a part of the extracellular domain, but lacking the transmembrane region and the cytoplasmic region of human TRAIL protein. In one embodiment, the human TRAIL polypeptide in the chimeric protein of the present invention is the amino acid sequence according to SEQ ID NO:2.

Examples of suitable human leucine zipper domains include leucine zipper domains from human c-fos, c-jun, c-myc, max, and mdx1 proteins.

In a preferred embodiment, the amino acid sequence of the human leucine zipper domain in the chimeric protein is the amino acid sequence according to SEQ ID NO:1.

In a preferred embodiment, the chimeric protein of the present invention has an amino acid sequence according to SEQ ID NO:3.

The present invention also provides an oligomeric complex having three molecules of the chimeric protein of the present invention strengthened together through the leucine zipper domain.

A DNA molecule encoding the chimeric protein of the present invention is also contemplated. In one embodiment, the DNA molecule has a nucleotide sequence according to SEQ ID NO:4.

In another aspect, the present invention provides an expression cassette comprising a transcriptional initiation region, a DNA molecule encoding the chimeric protein of the present invention under the transcriptional control of the transcriptional initiation region, and a transcriptional termination region. In one preferred embodiment, the expression cassette is a plasmid or virus.

Additionally, a cell and a transgenic animal comprising a DNA molecule encoding the chimeric protein of the present invention and expressing the chimeric protein are further provided. The cell can be a mammalian cell, insect cell, yeast or bacterial cell. The transgenic animal can be a transgenic goat, cow, etc.

In one example of the invention, a strain of E. coli is provided containing the DNA coding for the mentioned chimeric protein of this invention. The strain was deposited in Jun. 14, 2011 at China General Microbiological Culture Collection Center, or CGMCC), with the deposit number CGMCC No. 4953.

In addition, a method of producing a chimeric protein of the present invention is also provided, comprising the steps of: providing a cell or a transgenic animal comprising a DNA molecule encoding the chimeric protein, expressing said chimeric protein in said cell or transgenic animal, and isolating the chimeric protein.

In yet another aspect, the present invention provides the use of the chimeric protein of the present invention for the manufacture of a medicament for treating a disease, e.g., a human disease caused by uncontrolled cell growth such as cancer, psoriasis, autoimmune diseases, etc.

The animal experiments demonstrated that the control human TRAIL can inhibit tumor by 35.8%, while a chimeric protein of this invention completely eradicated this tumor. Furthermore, the treated nude mice were in significantly better health than their control counterparts treated with human TRAIL, indicating the chimeric protein of this invention carries reduced toxicity. In addition, the elimination rate of the chimeric protein of this invention is significantly lower, indicating a longer half life than that of the control TRAIL.

The foregoing and other advantages and features of the invention, and the manner in which the same are accomplished, will become more readily apparent upon consideration of the following detailed description of the invention taken in conjunction with the accompanying examples, which illustrate preferred and exemplary embodiments.

Biological Deposit

Strain name: *Escherichia coli*. The strain was deposited in Jun. 14, 2011 at China General Microbiological Culture Collection Center, or CGMCC). Address: 1-3 Beichen West Road, Institute of Microbiology, Chinese Academy of Sciences, Changyang District, Beijing. The deposit accession number is CGMCC No. 4953.

DETAILED DESCRIPTION OF THE INVENTION

Figure 1:
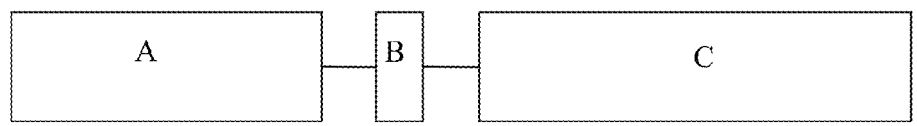
FIG. 1 shows a structural sketch of the chimeric protein. (A. the leucine zipper domain of human origin; B. The linker; C. The extracellular TRAIL domain.)

The invention provides a chimeric TRAIL protein, its encoding DNA, expression vectors, cells, transgenic animals and preparative methods and applications thereof in medical fields.

In accordance with the invention, a chimeric TRAIL has sequence from N-terminal to C-terminal direction, (1) a human leucine zipper domain; and (2) a human TRAIL protein, a human extracellular domain or a fragment of the extracellular domain that can bind to the death receptor DR4 (TRAIL-R1) or DR5 (TRAIL-R11).

Leucine zipper is a type of structural domain that can spontaneously oligomerize and is found in a variety of naturally occurring human proteins. This kind of structure is normally present in curved helix patterns and form oligomers through the characteristic alpha-helix interaction. For example, Haudenschild et al (Haudenschild D R, et al., J Biol Chem 270:23150-23154, 1995) described a kind of connective tissue protein martrilin, also called CMP, wherein three protein molecules form a homogeneous trimer through the action of their leucine zipper domains in the C terminal. Leucine zipper structural domains can further stabilize the trimeric structure of TRAIL.

The human leucine zipper domain in the chimeric protein of the present invention can be derived from any human protein. It is well known in the art that leucine zipper domains are found in a variety of naturally occurring human proteins. Leucine zipper domains can interact with each and dimerize or trimerize. Thus, the human leucine zipper domain included in the chimeric protein of the present invention can promote the oligomerization of the chimeric protein thereby increasing its stability. Preferably, the human leucine zipper domain is selected such that it promotes the trimerization of the chimeric protein. Examples of suitable human leucine zipper domains include leucine zipper domains from human c-fos, c-jun, c-myc, max and mdx1 proteins. Preferably, the human leucine zipper domain is the leucine zipper domain from human matrilin protein. In a preferred embodiment, the amino acid sequence of the human leucine zipper domain in the chimeric protein is the amino acid sequence according to SEQ ID NO:1.

The different amino acid sequences of the chimeric protein of the present invention can be directly linked together by peptide bonds. In one preferred embodiment, the amino acid sequence of the chimeric protein is according to SEQ ID NO:3.

The present invention also provides an oligomeric complex having three molecules of the chimeric protein of the present invention strengthened together through human TRAIL trimerization as well as intramolecular interaction of the leucine zipper domain in the chimeric protein. The stability and half life of the chimeric protein in the oligomer are both somewhat strengthened.

The invention in another aspect provides a DNA sequence encoding the protein mentioned above. Due to codon degeneracy, there might be many forms of DNA sequence that encodes the same protein as described in this invention. In one embodiment, the invention provides a DNA molecule that can encode a chimeric protein containing sequence according to SEQ ID NO:3. In one preferred embodiment, the DNA contains nucleotide sequence shown as SEQ ID NO:4.

In order to manufacture the chimeric protein and oligomer of this invention, DNA encoding the chimeric protein is incorporated into an expression cassette and then into an appropriate expression vector. The expression vector can be delivered into host cells or animals for the expression of the recombinant protein.

The expression cassette comprises at least these operably linked regions: 1) a transcriptional initiation region; 2) a DNA sequence encoding the chimeric protein of the present invention under the transcriptional control of the transcriptional initiation region; and 3) a transcriptional termination region. Based on different expression systems, the transcription initiation and termination region can be natural or artificially engineered, and suitable for transcription in eukaryotic or prokaryotic cells. These sequences are known in the art. The recombinant methods for combining an appropriate DNA fragment containing the initiation region and an appropriate DNA fragment containing the termination region and a DNA fragment encoding the chimeric protein are well known in the art. For example, appropriate restriction and ligation enzymes can be chosen for the cutting and ligation procedures.

extracellular part. Among these the linker region contains 2 cysteines, which in the active trimer structure form intermolecular disulfide bond between each other, strengthening the trimerization of TRAIL. Its sequence is shown as follows:

[SEQ ID NO: 3]
MEEDPCACESLVKFQAKVEGLLQALTRKLEAVSKRLAILENTVVGSTSEETISTVQEKQQN

ISPLVRERGPQRVAAHITGTRGRSNTLSSPNSKNEKALGRKINSWESSRSGHSFLSNLHLRN

GELVIHEKGFYYIYSQTYFRFQEEIKENTKNDKQMVQYIYKYTSYPDPILLMKSARNSCWS

KDAEYGLYSIYQGGIFELKENDRIFVSVTNEHLIDMDHEASFFGAFLVG

The expression cassette can be integrated into expression vectors, and then transfected into host cells or animals. In general, the expression vector also needs a replication initiation sequence and a selective marker. For example, for the expression in bacteria, plasmids are very useful. Many plasmids are known to the artisan in the field for this purpose, including but not limited to pET25b, pET15b etc. If the recombinant fusion protein is expressed through yeast cells, yeast expression vectors such as pPIC9, pAO815, pPICZ and the like can be used. If the expression is in mammalian cells, many suitable expression vectors are also available. For mammalian cell expression, the DNA sequence for the protein expression needs to be integrated into the mammalian cell genome. Examples of mammalian cell expression vectors include pcDNA3.1, pSI, and the like. For the expression of fusion proteins in animals, the technical methods of making transgenic animals (transgenic goat, cow, etc.) that contain the expression cassette are well known in the art. Suitable vectors such as pBLG can be used for making transgenic animals.

After obtaining the desired transfected host cells or transgenic animals, it is possible to express the chimeric protein of this invention under suitable conditions. Through various separation methods that are known in the art, the protein can be purified based on its physical and chemical properties and other characteristics. Examples of these methods are routine denaturing and renaturing treatment, centrifugation, sonication, membrane filtration, metal affinity chromatography, ionic chromatography, gel filtration chromatography, dialysis, HPLC and the like, and combination thereof.

The foregoing and other advantages and features of the invention will become more readily apparent upon consideration of the following detailed description of the invention taken in conjunction with the accompanying examples, which illustrate preferred and exemplary embodiments.

EXAMPLE 1

Construction of Fusion Protein

The inventors discovered through a large body of experiments that the constructed fusion protein LZ-TRAIL95 can eradicate tumor during treatments, and the status of the nude mice is significantly better than that of the group of mice administered with the control human TRAIL protein and that of the mice from the positive control, indicating that comapred to TRAIL, the fusion protein LZ-TRAIL95 is accompanied with reduced toxicity. In addition, the fusion protein has an in vivo half life of 218 minutes, significantly longer than that of the human origin TRAIL.

The fusion protein LZ-TRAIL95 comprises 3 parts: the linker region, the LZ (leucine zipper) region and the TRAIL The biggest problem encountered with LZ-TRAIL95 protein is mismatching of the disulfide bonds. In the non-reducing electrophoresis nonhomogeneous banding is obvious. Western blotting and peptide mapping proved that these bands are all LZ-TRAIL95. This issue could not be resolved with the addition of pharmaceutical additives and antioxidants.

In order to resolve the issue of disulfide mismatching in LZ-TRAIL95, the N terminal two Cys residues were changed to Ser and this resulted the construction of LZ-TRAIL95CS expression vector. The expressed LZ-TRAIL95CS protein sequence is shown in SEQ ID No. 3. Results indicated that these changes can greatly mitigate the nonhomogeneity issue occurring with the original LZ-TRAIL95.

After DTT removal, reverse phase C18 HPLC graph showed a purity of 90% for the protein. Compared with that of LZ-TRAIL95, the protein homogeneity is greatly improved. Molecular sieve showed that LZ-TRAIL95CS protein had a retaining time shorter than that of BSA(68 KD), as shown in Table 1, indicating the molecular weight of LZ-TRAIL95CS is larger than 68 KD and is likely in the form of active trimer.

TABLE 1

Reatining time of LZ-TRAIL95CS and BSA in SEC-HPLC

| protein | peak time (min) |
| --- | --- |
| LZ-TRAIL 95CS | 14.880 |
| BSA | 15.366 |

EXAMPLE 2

Expression Construct of the Chimeric Protein

Using a leucine zipper DNA fragment (LZ, a human leucine zipper structural domain, codon optimized for E. coli expression, synthesized by Shanghai Xuguan Biotech) as the template, the desired DNA piece was amplified by PCR with primers LZ1 and LZ2 (synthesized by Shanghai Sangon Biotech). In LZ1 the corresponding $6^{th}$ Cys and $8^{th}$ Cys were changed to Ser. LZ2 contains the 3' end of LZ fragment with additional sequence encoding GlySer as the linker peptide.

LZ1

(SEQ ID NO: 8)
5' GGAATTCCATATGGAGGAAGACCCGTCGGCCTCGGAAAGCCTGGTGA

AATTTC

-continued

LZ2:

(SEQ ID NO: 9)
5' CGCGGATCCGACAACGGTGTTTTCCAGG

TRAIL fragment was from TRAIL 95~281 amino acid region. It was amplified with PCR from human liver cDNA. Primers used were TRAIL1 and TRAIL2, synthesized (synthesized by Shanghai Sangon Biotech). Sequence analysis proved obtained sequence matches the one as listed in GenBank (NM_003810).

((SEQ ID NO: 10)
TRAIL1: 5' CGGGATCCACCTCTGAGGAAACCATTTCTACAG (SEQ ID NO: 11)
TRAIL2: 5' GGGAATTCTCATTAGCCAACTAAAAAGGCCCC

The PCR amplified LZ product was cut with restriction enzymes NdeI and BamHI (all DNA enzymes from Takara), TRAIL PCR product cut with BamHI and EcoRI, and pET25b (Novagen) empty plasmid with NdeI and EcoRI. These restriction digested fragments were retrieved from electrophoresis separation according to their sizes and ligated with T4 DNA ligase, resulting the recombinant expression vector pET-LZ-TRAIL for the TRAIL fusion protein. A map of this fusion protein is shown in FIG. 1.

The obtained pET-LZ-TRAIL plasmid was transformed by conventional methods into *E. coli* BL21(DE3) (Beijing Quanshijin Biotech.), and DNA plasmids isolated from Ampicilin resistant colonies were identified and confimed with restriction enzyme digestion and sequencing, The obtained positive colonies are the engineered strains for the expression of the corresponding protein.

EXAMPLE 3

Chimeric Protein Preparation

The *E. coli* colonies transformed with recombinant plasmid pET-LZ-TRAIL was incubated in LB medium (37° C.), and when cell density reached OD600≈0.8, 0.2 mM IPTG was added for expression induction. 6 hours later, cells were harvested by 5000 g (30') centrifugation.

Figure 2:
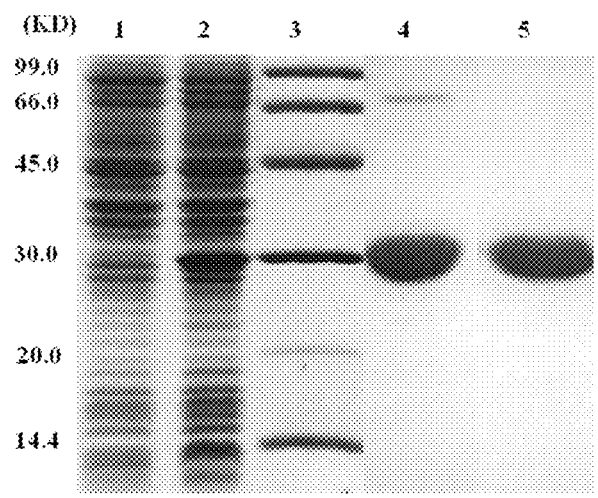
FIG. 2 shows the SDS-PAGE results of LZ-TRAIL protein expression and purification. (Lane 1: uninduced cell lysate; Lane 2: 0.2 mM IPTG induced cell lysate; Lane 3: protein molecular weight marker; Lane 4: metal-affinity purified LZ-TRAIL; Lane 5: LZ-TRAIL after ionic exchange purification. The arrow indicates the targeted protein.)

The harvested bacteria was suspended in Tris buffer (pH8.0), sonicated and the supernatant collected after 10,000 g centrifugation. The supernatant collected was applied to Ni-NTA(Qiagen) for metal affinity chromatography. The recombinant protein was eluted with 40 mM imidazole. The elutant was further purified through Q sepharose HP(GE) for ionic exchange chromatography to obtain highly pure recombinant LZ-TRAIL95CS protein. The results are shown in FIG. 2.

Figure 3:
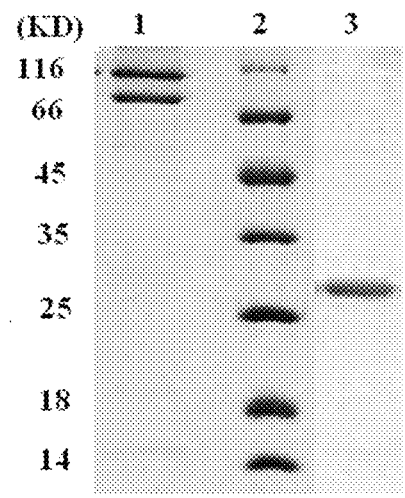
FIG. 3 shows reduced and non-reduced SDS-PAGE results of the purified LZ-TRAIL (no mutation). Lane 1: non-reduced SDS-PAGE result; Lane 2: protein molecular weight marker; Lane 3: reduced SDS-PAGE result; The arrow indicates the targeted protein.
Figure 4:
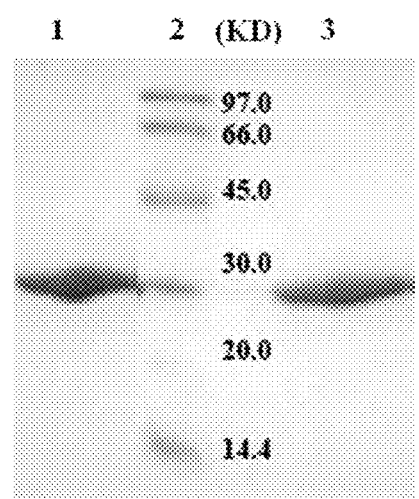
FIG. 4 shows reduced and non-reduced SDS-PAGE results of the purified LZ-TRAIL (with mutation). Lane 1: non-reduced SDS-PAGE result; Lane 2: protein molecular weight marker; Lane 3: reduced SDS-PAGE result; The arrow indicates the targeted protein.

Purified protein was subjected to reducing and non-reducing SDS-PAGE. Compared to the original fusion protein (before the Cys to Ser change at the 6th and 8th positions), the original fusion protein displayed two bands in SDS-PAGE, suggesting two kinds of disulfide bond formation and protein nonhomogeneity. However, this issue was resolved in the new chimeric protein after change of the two amino acids. These results are shown in FIGS. 3 and 4.

EXAMPLE 4

In Vivo Efficacy

Nude mice tumor model was established by subcutaneous innoculation of breast cancer cell MDA-MB231. In the tumor inhibition experiment mice were divided into the negative control group, the positive control group (human TRAIL extracellular region, amino acid sequence shown as SEQ ID NO:5) and the low dosage group (LZ-TRAIL, i.e., LZ-TRAIL95CS 5 mg/kg), high dosage group (LZ-TRAIL, 10 mg/kg), with 7 nude mice in each group. Drug was administered each day subcutaneously after the tumor reached 0.1 cm$^3$. Applied dosages were respectively 100 ug/animal/time (LZ-TRAIL low doasge), 200 ug/animal/time (LZ-TRAIL high dosage group) and 146 ug/animal/time (TRAIL, equalling the high dosage group in molar amount), for a total of 10 times drug administration. After 5 days of examination period mice were sacrificed and tumors were dissected and weighed. Tumor inhibition rate was estimated by the following formula:

tumor inhibition (%)=(control tumor weight−drug group tumor weight)/control tumor weight×100%

Figure 5:
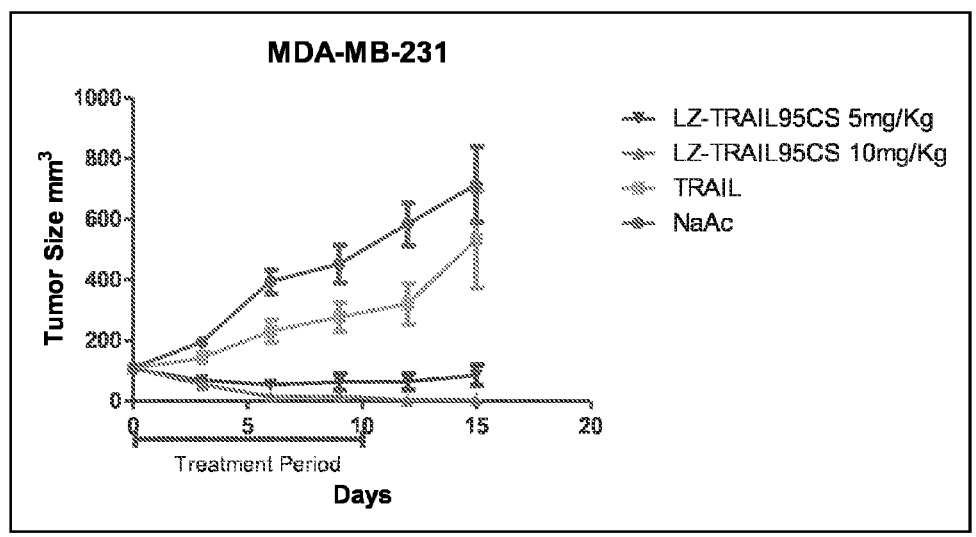
FIG. 5 shows the tumor growth curve of MDA-MB231 cancer cells in nude mice.
Figure 6:
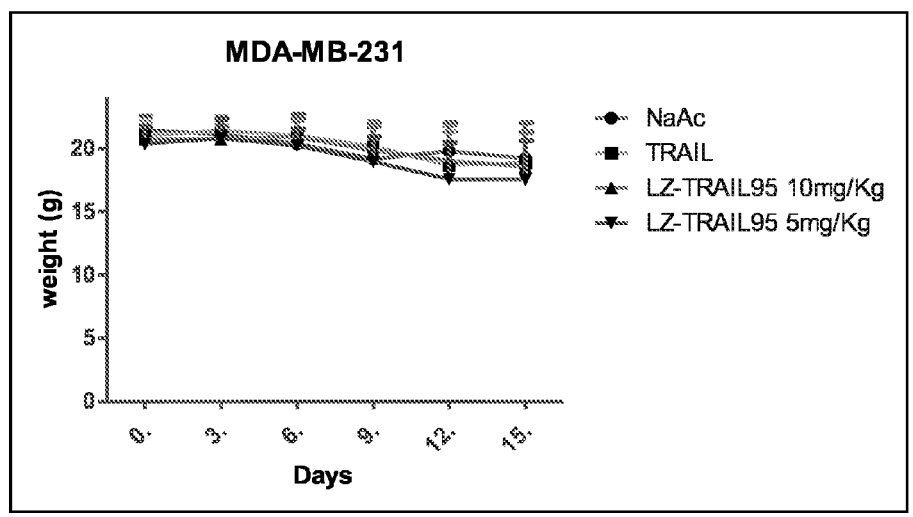
FIG. 6 shows the weight change curve of MDA-MB231 cancer cells in nude mice.

In the TRAIL group tumor inhibition rate was 35.8%, while in the group of LZ-TRAIL at comparable dosage tumor completely disappeared, even the low dosage LZ-TRAIL group saw a tumor inhibition rate of 94.5%. FIGS. 5 and 6 illustrate the tumor growth curve and weight change of the nude mice during the course of the experiment.

EXAMPLE 5

In Vivo Half Life of TRAIL

Figure 7:
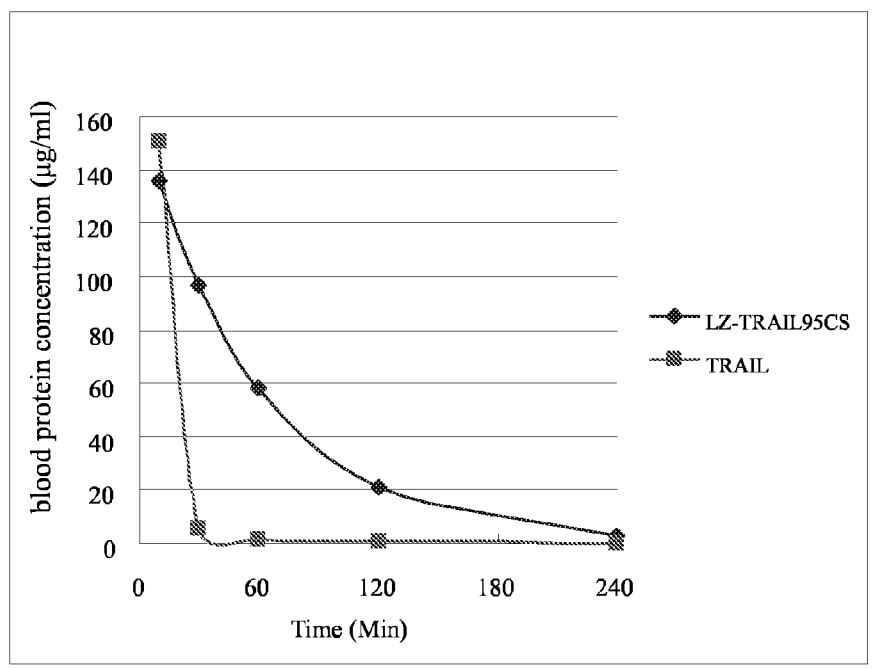
FIG. 7 shows the blood protein concentration curve of the chimeric protein and human TRAIL after the drug administration.

Estimation of in vivo half life was performed with two groups, the control group (TRAIL) and the experimental group (LZ-TRAIL, i.e., LZ-TRAIL95CS). Each group has two mice, each i.v. tail injected with 240 µg protein. After injection at time spots 0 min, 10 min, 30 min, 60 min, 120 min, 240 min, 1440 min 100 µl blood was drawn from eye sockets. Concentrations of TRAIL/LZ-TRAIL in the blood were estimated through ELISA. FIG. 7 shows the blood drug concentration curve.

The above results show that the TRAIL fusion protein of this invention, LZ-TRAIL95CS, can significantly reduce body protein clearance rate, increase its in vivo stability and significantly improve the efficacy. Therefore it potentially has broad future application.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be apparent that certain changes and modifications may be practiced within the scope of the appended claims.

What is claimed is:

1. A chimeric protein comprising from N-terminal to C-terminal direction:
    a human leucine zipper domain;
    a crosslinking region; and
    a full length human tumor necrosis factor-related apoptosis-inducing ligand (TRAIL) domain, human TRAIL extracellular domain, or a fragment thereof,
    wherein the crosslinking region consists of CC or GS, the full length human TRAIL domain comprises the amino acid sequence according to SEQ ID NO:6, the human TRAIL extracellular domain comprises the amino acid sequence according to SEQ ID NO:7, and the fragment of the human TRAIL extracellular domain comprises the amino acid sequence according to SEQ ID NO:2.

2. The chimeric protein of claim 1, wherein said human leucine zipper domain is a leucine zipper domain from c-jun, c-myc, max, mdx1 or human matrilin.

3. The chimeric protein of claim 1, wherein said leucine zipper domain comprises the amino acid sequence according to SEQ ID NO:1.

4. The chimeric protein of claim 1, wherein said chimeric protein comprises the amino acid sequence according to SEQ ID NO:3.

5. An oligomeric complex having three molecules of the chimeric protein of claim 1.

6. A DNA molecule encoding the chimeric protein of claim 1.

7. The DNA molecule of claim 6 comprising the nucleotide sequence according to SEQ ID NO:4.

8. An expression cassette comprising: a transcriptional initiation region; a DNA molecule encoding the chimeric protein according to claim 1 under the transcriptional control of said transcriptional initiation region; and a transcriptional termination region.

9. An expression construct comprising a DNA molecule encoding the chimeric protein of claim 1.

10. The expression construct of claim 9, wherein said construct is a plasmid or virus.

11. A cell culture or isolated cell expressing the chimeric protein of claim 1.

12. The cell culture or isolated cell of claim 11 is of mammalian, insect, yeast or bacteria.

13. The cell culture or isolated cell of claim 12, wherein said bacteria is an *E. coli* cell deposited at China General Microbiological Culture Collection Center, or CGMCC with accession number CGMCC No. 4953.

14. A method of producing a chimeric protein of claim 1, comprising:
    providing a cell expressing the chimeric protein of claim 1;
    expressing said chimeric protein in said cell; and
    isolating said chimeric protein.

* * * * *

SEQUENCE LISTING

<160> NUMBER OF SEQ ID NOS: 11

<210> SEQ ID NO 1
<211> LENGTH: 44
<212> TYPE: PRT
<213> ORGANISM: Artificial Sequence
<220> FEATURE:
<223> OTHER INFORMATION: human leucine zipper domain in the chimer ic
     protein

<400> SEQUENCE: 1

Met Glu Glu Asp Pro Ser Ala Ser Glu Ser Leu Val Lys Phe Gln Ala
1               5                   10                  15

Lys Val Glu Gly Leu Leu Gln Ala Leu Thr Arg Lys Leu Glu Ala Val
            20                  25                  30

Ser Lys Arg Leu Ala Ile Leu Glu Asn Thr Val Val
        35                  40

<210> SEQ ID NO 2
<211> LENGTH: 187
<212> TYPE: PRT
<213> ORGANISM: Homo sapiens

<400> SEQUENCE: 2

Thr Ser Glu Glu Thr Ile Ser Thr Val Gln Glu Lys Gln Gln Asn Ile
1               5                   10                  15

Ser Pro Leu Val Arg Glu Arg Gly Pro Gln Arg Val Ala Ala His Ile
            20                  25                  30

Thr Gly Thr Arg Gly Arg Ser Asn Thr Leu Ser Ser Pro Asn Ser Lys
        35                  40                  45

Asn Glu Lys Ala Leu Gly Arg Lys Ile Asn Ser Trp Glu Ser Ser Arg
    50                  55                  60

Ser Gly His Ser Phe Leu Ser Asn Leu His Leu Arg Asn Gly Glu Leu
65                  70                  75                  80

Val Ile His Glu Lys Gly Phe Tyr Tyr Ile Tyr Ser Gln Thr Tyr Phe
                85                  90                  95

Arg Phe Gln Glu Glu Ile Lys Glu Asn Thr Lys Asn Asp Lys Gln Met
            100                 105                 110

Val Gln Tyr Ile Tyr Lys Tyr Thr Ser Tyr Pro Asp Pro Ile Leu Leu
        115                 120                 125

Met Lys Ser Ala Arg Asn Ser Cys Trp Ser Lys Asp Ala Glu Tyr Gly
    130                 135                 140

Leu Tyr Ser Ile Tyr Gln Gly Gly Ile Phe Glu Leu Lys Glu Asn Asp
145                 150                 155                 160

Arg Ile Phe Val Ser Val Thr Asn Glu His Leu Ile Asp Met Asp His
                165                 170                 175

Glu Ala Ser Phe Phe Gly Ala Phe Leu Val Gly
            180                 185

<210> SEQ ID NO 3
<211> LENGTH: 233
<212> TYPE: PRT
<213> ORGANISM: Artificial Sequence
<220> FEATURE:
<223> OTHER INFORMATION: chimeric protein

<400> SEQUENCE: 3

Met Glu Glu Asp Pro Ser Ala Ser Glu Ser Leu Val Lys Phe Gln Ala
1               5                   10                  15

```
Lys Val Glu Gly Leu Leu Gln Ala Leu Thr Arg Lys Leu Glu Ala Val
             20                  25                  30
Ser Lys Arg Leu Ala Ile Leu Glu Asn Thr Val Val Gly Ser Thr Ser
         35                  40                  45
Glu Glu Thr Ile Ser Thr Val Gln Glu Lys Gln Gln Asn Ile Ser Pro
 50                  55                  60
Leu Val Arg Glu Arg Gly Pro Gln Arg Val Ala Ala His Ile Thr Gly
 65                  70                  75                  80
Thr Arg Gly Arg Ser Asn Thr Leu Ser Ser Pro Asn Ser Lys Asn Glu
                 85                  90                  95
Lys Ala Leu Gly Arg Lys Ile Asn Ser Trp Glu Ser Ser Arg Ser Gly
            100                 105                 110
His Ser Phe Leu Ser Asn Leu His Leu Arg Asn Gly Glu Leu Val Ile
        115                 120                 125
His Glu Lys Gly Phe Tyr Tyr Ile Tyr Ser Gln Thr Tyr Phe Arg Phe
    130                 135                 140
Gln Glu Glu Ile Lys Glu Asn Thr Lys Asn Asp Lys Gln Met Val Gln
145                 150                 155                 160
Tyr Ile Tyr Lys Tyr Thr Ser Tyr Pro Asp Pro Ile Leu Leu Met Lys
                165                 170                 175
Ser Ala Arg Asn Ser Cys Trp Ser Lys Asp Ala Glu Tyr Gly Leu Tyr
            180                 185                 190
Ser Ile Tyr Gln Gly Gly Ile Phe Glu Leu Lys Glu Asn Asp Arg Ile
        195                 200                 205
Phe Val Ser Val Thr Asn Glu His Leu Ile Asp Met Asp His Glu Ala
    210                 215                 220
Ser Phe Phe Gly Ala Phe Leu Val Gly
225                 230

<210> SEQ ID NO 4
<211> LENGTH: 699
<212> TYPE: DNA
<213> ORGANISM: Artificial Sequence
<220> FEATURE:
<223> OTHER INFORMATION: nucleotide sequence encoding the chimeric
      protein containing sequence according to SEQ ID NO: 3

<400> SEQUENCE: 4
atggaggaag acccgtcggc ctcggaaagc ctggtgaaat tcaggccaa agtggagggt      60 ctgttacagg ccctgacccg caaattggaa gcagtgagca acgcttagc aatcctggaa     120 aacaccgttg tcggatccac ctctgaggaa accatttcta cagttcaaga aaagcaacaa    180
aatatttctc ccctagtgag agaaagaggt cctcagagag tagcagctca cataactggg    240
accagaggaa gaagcaacac attgtcttct ccaaactcca agaatgaaaa ggctctgggc    300
cgcaaaataa actcctggga atcatcaagg agtgggcatt cattcctgag caacttgcac    360
ttgaggaatg gtgaactggt catccatgaa aagggttttt actacatcta ttcccaaaca    420
tactttcgat tcaggagga aataaaagaa aacacaaaga cgacaaaca atggtccaa       480 tatatttaca atacacaag ttatcctgac cctatattgt tgatgaaaag tgctagaaat     540
agttgttggt ctaaagatgc agaatatgga ctctattcca tctatcaagg gggaatattt    600
gagcttaagg aaaatgacag aatttttgtt tctgtaacaa atgagcactt gatagacatg    660
gaccatgaag ccagtttttt cggggccttt ttagttggc                           699

<210> SEQ ID NO 5
```

```
<211> LENGTH: 168
<212> TYPE: PRT
<213> ORGANISM: Homo sapiens

<400> SEQUENCE: 5

Val Arg Glu Arg Gly Pro Gln Arg Val Ala Ala His Ile Thr Gly Thr
1               5                   10                  15

Arg Gly Arg Ser Asn Thr Leu Ser Ser Pro Asn Ser Lys Asn Glu Lys
            20                  25                  30

Ala Leu Gly Arg Lys Ile Asn Ser Trp Glu Ser Ser Arg Ser Gly His
        35                  40                  45

Ser Phe Leu Ser Asn Leu His Leu Arg Asn Gly Glu Leu Val Ile His
    50                  55                  60

Glu Lys Gly Phe Tyr Tyr Ile Tyr Ser Gln Thr Tyr Phe Arg Phe Gln
65                  70                  75                  80

Glu Glu Ile Lys Glu Asn Thr Lys Asn Asp Lys Gln Met Val Gln Tyr
                85                  90                  95

Ile Tyr Lys Tyr Thr Ser Tyr Pro Asp Pro Ile Leu Leu Met Lys Ser
            100                 105                 110

Ala Arg Asn Ser Cys Trp Ser Lys Asp Ala Glu Tyr Gly Leu Tyr Ser
        115                 120                 125

Ile Tyr Gln Gly Gly Ile Phe Glu Leu Lys Glu Asn Asp Arg Ile Phe
    130                 135                 140

Val Ser Val Thr Asn Glu His Leu Ile Asp Met Asp His Glu Ala Ser
145                 150                 155                 160

Phe Phe Gly Ala Phe Leu Val Gly
                165

<210> SEQ ID NO 6
<211> LENGTH: 281
<212> TYPE: PRT
<213> ORGANISM: Homo sapiens

<400> SEQUENCE: 6

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175
```

```
His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
            275                 280

<210> SEQ ID NO 7
<211> LENGTH: 241
<212> TYPE: PRT
<213> ORGANISM: Homo sapiens

<400> SEQUENCE: 7

Glu Leu Lys Gln Met Gln Asp Lys Tyr Ser Lys Ser Gly Ile Ala Cys
1               5                   10                  15

Phe Leu Lys Glu Asp Asp Ser Tyr Trp Asp Pro Asn Asp Glu Glu Ser
            20                  25                  30

Met Asn Ser Pro Cys Trp Gln Val Lys Trp Gln Leu Arg Gln Leu Val
        35                  40                  45

Arg Lys Met Ile Leu Arg Thr Ser Glu Glu Thr Ile Ser Thr Val Gln
50                  55                  60

Glu Lys Gln Gln Asn Ile Ser Pro Leu Val Arg Glu Arg Gly Pro Gln
65                  70                  75                  80

Arg Val Ala Ala His Ile Thr Gly Thr Arg Gly Arg Ser Asn Thr Leu
                85                  90                  95

Ser Ser Pro Asn Ser Lys Asn Glu Lys Ala Leu Gly Arg Lys Ile Asn
            100                 105                 110

Ser Trp Glu Ser Ser Arg Ser Gly His Ser Phe Leu Ser Asn Leu His
        115                 120                 125

Leu Arg Asn Gly Glu Leu Val Ile His Glu Lys Gly Phe Tyr Tyr Ile
130                 135                 140

Tyr Ser Gln Thr Tyr Phe Arg Phe Gln Glu Glu Ile Lys Glu Asn Thr
145                 150                 155                 160

Lys Asn Asp Lys Gln Met Val Gln Tyr Ile Tyr Lys Tyr Thr Ser Tyr
                165                 170                 175

Pro Asp Pro Ile Leu Leu Met Lys Ser Ala Arg Asn Ser Cys Trp Ser
            180                 185                 190

Lys Asp Ala Glu Tyr Gly Leu Tyr Ser Ile Tyr Gln Gly Gly Ile Phe
        195                 200                 205

Glu Leu Lys Glu Asn Asp Arg Ile Phe Val Ser Val Thr Asn Glu His
210                 215                 220

Leu Ile Asp Met Asp His Glu Ala Ser Phe Phe Gly Ala Phe Leu Val
225                 230                 235                 240

Gly

<210> SEQ ID NO 8
```

```
<211> LENGTH: 53
<212> TYPE: DNA
<213> ORGANISM: Artificial Sequence
<220> FEATURE:
<223> OTHER INFORMATION: LZ1

<400> SEQUENCE: 8
ggaattccat atggaggaag acccgtcggc ctcggaaagc ctggtgaaat ttc         53

<210> SEQ ID NO 9
<211> LENGTH: 28
<212> TYPE: DNA
<213> ORGANISM: Artificial Sequence
<220> FEATURE:
<223> OTHER INFORMATION: LZ2

<400> SEQUENCE: 9
cgcggatccg acaacggtgt tttccagg                                     28

<210> SEQ ID NO 10
<211> LENGTH: 33
<212> TYPE: DNA
<213> ORGANISM: Artificial Sequence
<220> FEATURE:
<223> OTHER INFORMATION: TRAIL1

<400> SEQUENCE: 10
cgggatccac ctctgaggaa accatttcta cag                               33

<210> SEQ ID NO 11
<211> LENGTH: 32
<212> TYPE: DNA
<213> ORGANISM: Artificial Sequence
<220> FEATURE:
<223> OTHER INFORMATION: TRAIL2

<400> SEQUENCE: 11
gggaattctc attagccaac taaaaaggcc cc                                32
```